US010041828B2

(12) United States Patent
Broussais-Colella et al.

(10) Patent No.: US 10,041,828 B2
(45) Date of Patent: Aug. 7, 2018

(54) METHOD FOR INSPECTION BY THE TRANSMISSION OF ULTRASOUNDS

(71) Applicant: SNECMA, Paris (FR)

(72) Inventors: Nicolas Broussais-Colella, Mooissy-Cramayel (FR); Jean-Yves Chatellier, Moissy-Cramayel (FR); Jeremy Duval, Moissy-Cramayel (FR)

(73) Assignee: SNECMA, Paris (FR)

( * ) Notice: Subject to any disclaimer, the term of this patent is extended or adjusted under 35 U.S.C. 154(b) by 145 days.

(21) Appl. No.: 14/893,908

(22) PCT Filed: May 22, 2014

(86) PCT No.: PCT/FR2014/051202
§ 371 (c)(1),
(2) Date: Nov. 24, 2015

(87) PCT Pub. No.: WO2014/191661
PCT Pub. Date: Dec. 4, 2014

(65) Prior Publication Data
US 2016/0109283 A1 Apr. 21, 2016

(30) Foreign Application Priority Data

May 30, 2013 (FR) ..................... 13 54956

(51) Int. Cl.
*G01N 29/44* (2006.01)
*G01N 29/04* (2006.01)
(Continued)

(52) U.S. Cl.
CPC ............. *G01H 1/003* (2013.01); *G01N 29/11* (2013.01); *G01N 29/44* (2013.01);
(Continued)

(58) Field of Classification Search
CPC ........ G01N 29/04; G01N 29/11; G01N 29/44; G01N 29/4463; G01N 29/4427;
(Continued)

(56) References Cited

U.S. PATENT DOCUMENTS 4,004,454 A 1/1977 Matay
4,462,082 A * 7/1984 Thiele .................... G01N 29/30
367/13
(Continued)

FOREIGN PATENT DOCUMENTS

DE 10258336 4/2004
FR 2959817 11/2011

OTHER PUBLICATIONS

French Search Report and Written Opinion, dated Feb. 20, 2014, French Application No. 1354956.
(Continued)

*Primary Examiner* — Helen Kwok
(74) *Attorney, Agent, or Firm* — Womble Bond Dickinson (US) LLP

(57) ABSTRACT

A method for inspecting an object by ultrasound transmission, including sweeping an ultrasound beam over a reference part that has the same geometry as the object to be inspected, and measuring the amplitude transmitted through the part to obtain a mapping thereof. The ultrasound beam is amplified with a reference gain. The method further includes determining gain corrections to be added to the reference gain at certain points during the sweeping of the reference part to obtain an ultrasound beam amplitude transmitted through the part which is constant at each point of the mapping, and sweeping an ultrasound beam over the object to be inspected and measuring the transmitted amplitude.

(Continued)

The gain applied to the various points during the sweeping corresponds to the reference gain corrected on the basis of said corrections.

12 Claims, 5 Drawing Sheets

(51) Int. Cl.
*G01H 1/00* (2006.01)
*G01N 29/11* (2006.01)

(52) U.S. Cl.
CPC ............... *G01N 29/4463* (2013.01); *G01N 2291/0231* (2013.01); *G01N 2291/0289* (2013.01); *G01N 2291/044* (2013.01); *G01N 2291/048* (2013.01)

(58) Field of Classification Search
CPC ...... G01N 29/26; G01N 29/30; G01N 29/265; G01N 29/0609
See application file for complete search history.

(56) References Cited

U.S. PATENT DOCUMENTS

| | | | | |
|---|---|---|---|---|
| 4,545,251 A | * | 10/1985 | Uchida | G01N 29/0609 73/1.82 |
| 4,607,341 A | * | 8/1986 | Monchalin | G01N 25/72 702/134 |
| 5,241,473 A | * | 8/1993 | Ishihara | A61B 8/06 348/163 |
| 5,777,891 A | * | 7/1998 | Pagano | G01N 29/0609 702/39 |
| 6,220,099 B1 | * | 4/2001 | Marti | G01N 29/226 73/633 |
| 6,394,646 B1 | * | 5/2002 | Ringermacher | G01B 11/06 250/330 |
| 8,668,434 B2 | * | 3/2014 | Karpman | F01D 21/003 415/7 |
| 2006/0122506 A1 | * | 6/2006 | Davies | A61B 8/14 600/437 |
| 2007/0051177 A1 | | 3/2007 | Gifford et al. | |
| 2009/0277269 A1 | * | 11/2009 | Sarr | G01N 29/07 73/620 |
| 2009/0301198 A1 | * | 12/2009 | Sohn | G01N 29/069 73/598 |
| 2014/0114191 A1 | * | 4/2014 | Sankar | A61B 8/14 600/447 |
| 2015/0316513 A1 | * | 11/2015 | Grimard | G01N 29/4427 702/103 |

OTHER PUBLICATIONS

International Search Report and Written Opinion with English Language Translation, dated Aug. 29, 2014, Application No. PCT/FR2014/051202.

* cited by examiner

- - Prior Art - -

-- Prior Art --

-- Prior Art --

FIG. 6
FIG. 7a                FIG. 7b
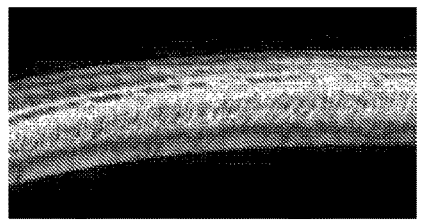      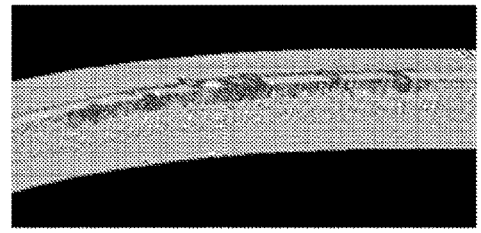
FIG. 8a                FIG. 8b
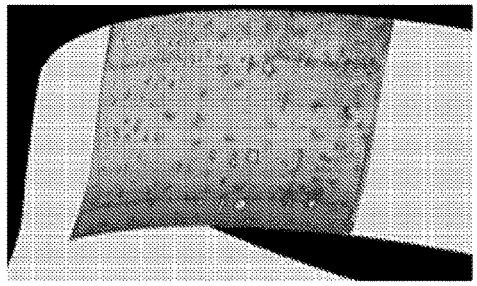      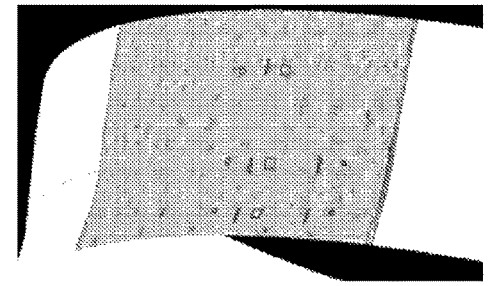

METHOD FOR INSPECTION BY THE TRANSMISSION OF ULTRASOUNDS

FIELD OF THE INVENTION

The invention relates to the field of non-destructive inspection methods of objects by ultrasound transmission to detect internal anomalies, such as porosities, delaminations, cracks, etc. present in the volume of the inspected object or adhesion defects in the event where the inspected object is formed by connecting several pieces.

The invention applies especially to the inspection of pieces having complex geometry such as blades and turbomachine blade casings.

PRIOR ART

Different non-destructive control techniques by ultrasound are already known. A known technique is control by reflection, during which scanning of an object to be inspected is performed with an ultrasound beam with determined gain, and the amplitude of the reflected beam is measured by the object to detect any alterations in the internal structure of the object.

However, the method of control by ultrasound reflection is not adapted to objects made of material substantially absorbing the ultrasound, such as for example composite materials. Yet, use is now made of composite materials to make turbomachine elements, such as blades or blade casings for example.

In this case, a more adapted inspection method is ultrasound control by transmission using representation of "C-Scan" type. This involves access to two opposite faces of the piece to be controlled. The receiver is then placed opposite the transmitter and it recovers the energy which has been transmitted via the piece. Reflectors such as interfaces or anomalies will be detected by a drop in this energy, but it is not possible to locate it in the thickness of the piece.

From this amplitude measurement, mapping is then carried out representing a projection of the inspected object in the direction of the ultrasound beam, whereof each point is coloured as a function of amplitude. Such mapping, made at the level of a leading edge of a turbomachine blade, is illustrated in FIG. 4a. The darker areas correspond to areas where the amplitude of the ultrasound beam transmitted is weak, that is, where attenuation is high.

The decrease in amplitude of the ultrasound beam depends both on the thickness of material passed through and any defects encountered; for example, if a cavity is found in the inspected object, on the path of the ultrasound beam, the ultrasound beam is not transmitted via this cavity, and the amplitude transmitted through this cavity is therefore highly reduced relative to initial emission amplitude.

In the event where the inspected object has a complex geometry, which is the case for example of turbomachine blades, or blade casings, it is therefore impossible, with the inspection method by ultrasound transmission, to make the difference between an area having a defect and an area where the thickness of material to be passed through is considerable, or even misalignment of the probes due to the geometry of the piece.

For example, in FIG. 5a, the left part of the figure corresponds to the root of the blade and the right part corresponds to the head of the blade, this blade being illustrated in FIG. 1. The left end of the mapping in FIG. 5a corresponding to the root of the blade has dark colouring, indicating strong absorption of the ultrasound at this level of the blade. This strong absorption can be linked to a defect in this root or stem from the thickness of the blade at this level, but it is not possible to determine it with this mapping.

There is therefore a need for an inspection method of an object which gets over the complexity of the geometry of the inspected object, and identifies defects in the structure of the inspected object independently of the thickness of the object.

For this to occur, a method could comprise multiple scans of the same piece with ultrasound beams having a different gain at each scan and each pitch. However, since all the pieces must be inspected before being used, this method would cause excessive time loss.

PRESENTATION OF THE INVENTION

The aim of the invention is to propose an inspection method of an object to immediately identify defects present in the structure of the object.

Another aim of the invention is to be able to use any geometry of the inspected object.

In this respect, the aim of the invention is an inspection method of an object by ultrasound transmission, in which scanning of said object is carried out by an ultrasound beam and measuring of the amplitude of the ultrasound beam transmitted via said object, said measuring comprising conversion of the ultrasound beam into an electrical signal, the application of an amplification gain to said signal and measuring of the amplitude of said signal, to deduce therefrom a mapping in which each point of a projection surface of said object according to the direction of exposure is associated to the amplitude of the ultrasound beam transmitted to said point via said object, the method being characterized in that it comprises the steps consisting of:

carrying out said scanning and said amplitude measurement on a reference piece having a geometry identical to the object to be inspected, to deduce therefrom a mapping of said piece, the amplification gain applied for the amplitude measurement being a predetermined reference gain, determining, for a plurality of points of the mapping of the reference piece, gain corrections to be made to the reference gain at the corresponding points of the scanning to obtain a constant amplitude of the ultrasound beam transmitted via the reference piece for all the points of the mapping, carrying out said scanning and said amplitude measurement on the object to be inspected by applying to the different points of the scanning an amplification gain corresponding to the reference gain corrected from gain corrections previously determined.

Advantageously, but optionally, the method according to the invention further has at least one of the following characteristics:

mapping of the object is deduced from said amplitude measurement on the object to be inspected and the resulting mapping is analysed to detect any anomaly as to the amplitude transmitted via the object.

the object to be inspected and the reference piece are axisymmetrical, the direction of exposure of the ultrasound beam is radial relative to the axis of symmetry, and the reference piece is scanned according to a line of said piece at the intersection of the surface of the reference piece with a radial plane, the object to be inspected and the reference piece comprise composite material.

the constant amplitude transmitted via the reference piece is greater than 60% of the amplitude of the ultrasound beam emitted, and is advantageously between 70 and 90% of said amplitude, and preferably equal to 80% of said amplitude.

the gain correction to be made to the reference gain at a point of the scanning is determined simultaneously to the scanning of the corresponding point of the reference piece.

The invention also relates to use of the inspection method for the inspection of a blade, especially a blade formed from composite material and further comprising a metal reinforcement stuck to its leading edge, said method for detecting any adhesion anomalies or even for the inspection of a blade casing.

Another aim of the invention is an inspection system of an object by ultrasound transmission for carrying out the above inspection method, comprising:

an emission probe of an ultrasound beam and control means of the scanning of the probe, adapted for performing scanning of said object by an ultrasound beam emitted by the probe, an ultrasound receiver, adapted to convert the ultrasound beam transmitted via said object into an electrical signal, and a processing unit, comprising an amplifier adapted to apply an amplification gain to the electrical signal obtained by the receiver, and a control unit configured to measure the amplitude of the amplified signal and to deduce from said amplitude measurement a mapping in which each point of a projection surface of said object according to the direction of exposure is associated to the amplitude transmitted to said point via said object, the system being characterized in that the control unit is further adapted to determine, for a plurality of points of a mapping performed from the scanning of a reference piece by an ultrasound beam at a predetermined reference gain, gain corrections to be made to the reference gain at the corresponding points of the scanning to obtain a constant amplitude ($A_c$) transmitted via the reference piece for all the points of the mapping, and to control the amplifier in order to apply, during the scanning and said amplitude measurement on the object to be inspected, to the different points of the scanning of the ultrasound beam, an amplification gain corresponding to the reference gain corrected as a function of the gain corrections thus determined.

The proposed inspection method allows obviating the geometry of an object, so that decreases in energy illustrated on the mapping resulting from the inspection are linked only to structural defects of the object.

Indeed, using a reference piece, which is known to be devoid of defects, adapts the gain of the ultrasound reception signal beam to the thickness of the inspected object at the level of the point of exposure. In this way, the amplitude of the ultrasound beam is modified so that the object seems to exhibit constant thickness. It eventuates that the variations in transmitted amplitude can originate only from defects of the inspected object, the variations linked to the thickness of the object being eliminated.

This method therefore inspects faster and with improved reliability pieces having a complex geometry.

DESCRIPTION OF FIGURES

Other characteristics, aims and advantages of the present invention will emerge from the following detailed description, with respect to the appended figures, given by way of non-limiting examples and in which:

FIG. 6 illustrates an axial profile of a turbomachine blade casing, FIGS. 7a and 7b illustrate respectively the mappings of a blade casing flange obtained before and after correction of the gain of the ultrasound reception signal, FIGS. 8a and 8b illustrate respectively the mappings of an inspected blade casing obtained before and after correction of the gain of the ultrasound reception signal.

DETAILED DESCRIPTION OF AT LEAST ONE EMBODIMENT OF THE INVENTION

Figure 2:
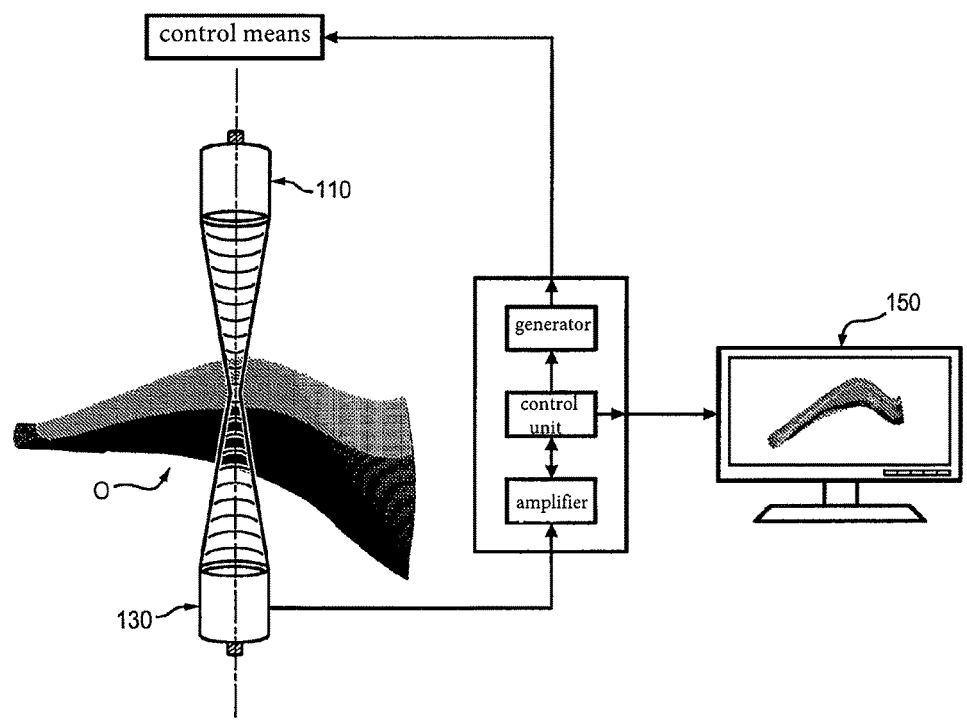
FIG. 2 schematically illustrates an inspection system by ultrasound transmission.

In reference to FIG. 2, this schematically illustrates an inspection system 100 of an object O by ultrasound transmission used for carrying out the method described hereinbelow.

This system comprises an emission probe 110 of an ultrasound beam which is moved according to a predetermined path by control means 120 of the scanning of said probe.

The receiver 130 is positioned on the other side of the probed object O.

The probe 110 and the receiver 130 are piezoelectric transducers, capable of converting an electrical signal into a mechanical wave and vice versa. Consequently, the roles of the probe and of the receiver can be reversed.

In this case, the probe is excited electrically by a signal supplied by a generator 141 of a processing unit 140 for emitting ultrasound waves, and the receiver 130 converts the ultrasound waves being propagated via the probed object into an electrical signal.

The amplitude of the ultrasound beam transmitted via the object is measured as follows. The electrical signal converted by the receiver is transmitted to the processing unit 140 which comprises an amplifier 142 for amplifying the electrical signal with a preferred gain, said gain corresponding to a gain in amplitude of the ultrasound beam transmitted via the object O. The processing unit further comprises a control unit 143, which advantageously can be a processor, which then measures the amplitude of the now amplified electrical signal, said amplitude corresponding to the amplitude of the ultrasound beam.

The control unit 143 is further adapted to associate at each point of the scanning of the probed object the amplitude of the ultrasound beam transmitted via the object at the level of said point of the scanning. In this case, the word "mapping" means this relating of points with the respective amplitude, whether or not followed by two-dimensional display of the object representing each point of the scanning in a particular colour dependent on its transmitted amplitude.

Advantageously, but optionally, the inspection system 100 further comprises a display 150 for showing said mapping.

The control unit 142 is also adapted to control the gain made by the amplifier 142 to the ultrasound beam received by the receiver 130, as will be shown hereinbelow.

Figure 3:
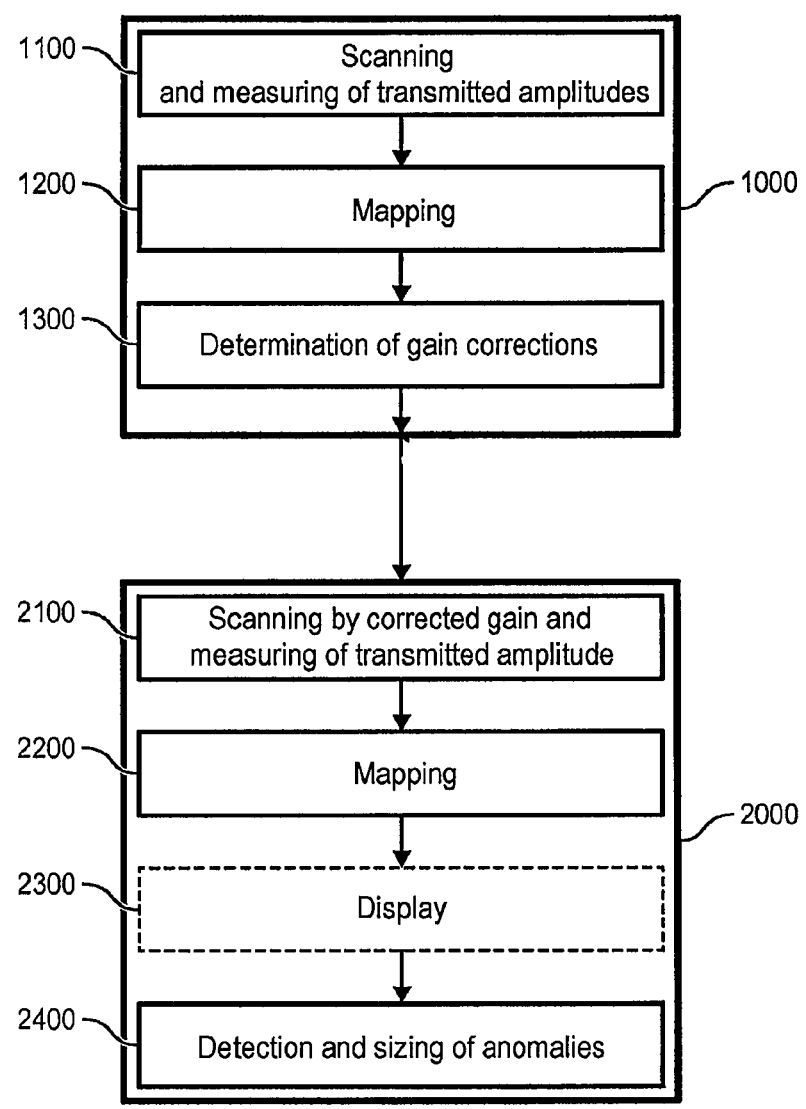
FIG. 3 illustrates the principal steps of an inspection method by ultrasound transmission.

In reference to FIG. 3, this shows the principal steps of an inspection method of an object by ultrasound transmission, performed by the system previously described.

This method comprises carrying out a control of an object by ultrasound transmission of "C-Scan" type, comprising a first measurement step during which an object to be inspected is scanned with an ultrasound beam, by amplifying the signal received from the ultrasound transmitted via the object with a determined gain, and the amplitude of the ultrasound beam transmitted via the object is measured after amplification, and a second interpretation step, during which, from these amplitude measurements, two-dimensional mapping of the object is set up, this mapping being a projection of the inspected object according to the direction of exposure of the ultrasound beam. The object y is represented in colours or in shades of grey, each point of the mapping being associated by its colour with the amplitude of the ultrasound beam transmitted via said object.

This control is first conducted on a reference piece during an initialisation step 1000 to deduce, for this piece, gain corrections of the signal transmitted to be made to the gain of the amplifier 142 so that the amplitude of the ultrasound transmitted via said piece is constant.

Then the method comprises an actual inspection step 2000 of each object O to be inspected, comprising performing a control of "C-scan" type by using the corrected gain from corrections determined during the initialisation step as ultrasound reception gain.

The initialisation step 1000 taken on a reference piece will now be described in detail.

The reference piece is a piece having the same geometry, that is, the same dimensions, as the object to be inspected. For example, if the object to be inspected is a turbomachine blade, the reference piece is a blade of the same design.

Also the reference piece must have been selected and controlled by other means for verifying that it comprises no defect.

During a first substep 1100, the reference piece is scanned by an ultrasound beam emitted by the probe with a predetermined amplitude $A_s$.

The receiver receives the ultrasound beam and transmits a corresponding electrical signal to the processing unit.

The control unit 143 of the processing unit measures the transmitted amplitude $A_t$ of the ultrasound for a predetermined reference gain $P_{ref}$ of the amplifier 142 via said piece at each point of the scanning and deduces therefrom during a substep 1200 a mapping linking the amplitude transmitted at the level of said point to each point of the scanning.

The control unit determines during a substep 1300, at each point of the scanning, the amplification gain of the received energy $G_c$ which should be selected so that the amplitude of the ultrasound transmitted via said piece is constant for all the points of the scanning, and deduces therefrom a list of corrections to be made to the reference gain $G_{ref}$ at each point of the scanning to obtain the corrected gain $G_c$.

This determination of gain corrections can be made once all the scanning of the piece has been completed. Alternatively, and preferably, determination of the gain corrections can be made in real time, that is, determination and application of a gain correction to be made to the reference gain $G_{ref}$ at the level of a point of the scanning of the piece is determined at the time of scanning of said point by the control unit 143.

The constant amplitude $A_c$ transmitted with the corrected gain is preferably greater than 60% of the amplitude $A_s$ of the ultrasound emitted by the probe, to then allow good resolution of the acquired data. Advantageously, the amplitude with the corrected gain is between 70 and 90% of the amplitude $A_s$ of the ultrasound emitted, and preferably of the order of 80%. This represents a good compromise between the amplitude and the resolution obtained.

This produces a table similar to that shown below, in which each point of the scanning is linked to a gain correction as a function of the amplitude transmitted during control of the reference piece:

| Point | 1 | 2 | 3 | 4 | ... | N |
|---|---|---|---|---|---|---|
| Energy/amplitude $A_t$ transmitted before correction in % of amplitude $A_s$ | 95 | 80 | 70 | 60 | ... | 5 |
| Correction in decibels (dB) | −X | +0 | +Y | +Z | ... | +P |
| Energy/amplitude transmitted after correction $A_c$ in % of amplitude $A_s$ | 80 | 80 | 80 | 80 | 80 | 80 |

The fact of obtaining constant corrected transmitted amplitude $A_c$ for the reference piece avoids taking into account variations in thickness of the piece at the level of the different points of scanning. Consequently, by later applying a corrected gain $G_c$ from said corrections to an object controlled having the same geometry as the reference piece, the only variations of the amplitude transmitted will result directly from defects in the structure of the controlled object.

Figure 4A:
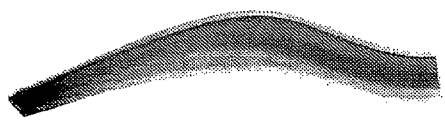
FIGS. 4a and 4b illustrate respectively the mappings of a reference blade obtained before and after correction of the gain of the ultrasound reception signal, FIGS. 5a and 5b (FIG. 5a already described) illustrate respectively the mappings of an inspected blade obtained before and after correction of the gain of the ultrasound reception signal.
Figure 4B:
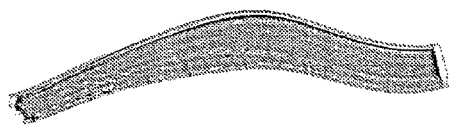

FIG. 4a illustrates a mapping obtained for the reference piece by applying the reference gain $G_{ref}$ of the ultrasound, and FIG. 4b shows the corrected gain $G_c$. The mapping clearly shows that the variations in the amplitude transmitted due to variations in thickness of the piece are eliminated, and that the transmitted amplitude $A_c$ after correction is constant.

In reference to FIG. 3, the inspection step 2000 of an object will now be described.

As indicated previously, this object must have the same geometry and the same structure as the reference piece so that the list of corrections set for the scanning points is valid.

During a substep 2100, the object is scanned by an ultrasound beam, the gain of which at each point of the scanning is the corrected gain $G_c$, that is, the reference gain $G_{ref}$ to which the corrections determined earlier have been added.

The receiver senses the ultrasound beam and the control unit measures the amplitude of the amplified signal with the corrected gain.

During a substep 2200, the control unit 143 performs mapping of the probed object, by associating with each point of the scanning the amplitude of the ultrasound transmitted via the object and received by the receiver. Advantageously, this mapping is illustrated on the display during a step 2300, each point of the scanning being represented by a colour or a shade of grey representative of the attenuation rate of the transmitted amplitude, or of the transmitted amplitude itself.

Figure 5A:
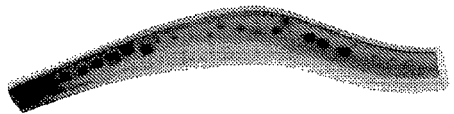
Figure 5B:
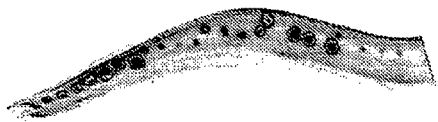

FIGS. 5a and 5b illustrate the mappings obtained for a turbomachine blade, respectively with a non-corrected and corrected reception gain of the ultrasound.

Figure 1:
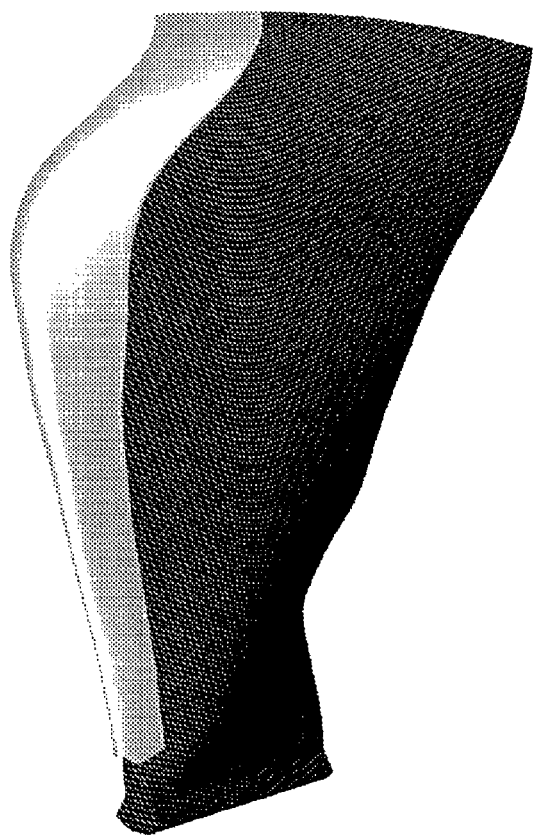
FIG. 1, already described, illustrates a turbomachine blade.

This turbomachine blade 10 is made of composite material and has a metal reinforcement 11 on its leading edge, as shown in FIG. 1. The inspection method is used especially for identifying adhesion defects of the reinforcement on the leading edge. In this respect, adhesion defects have been simulated in the tested blade of FIGS. 5a and 5b by positioning inserts made of absorbent material between the leading edge of the blade and the metal reinforcement.

FIG. 5b shows that the inserts are much more visible, and their shape is clearer, once the gain corrections are applied to the ultrasound reception signal.

Analysis of the resulting mapping, performed during a step 2400, either by an operator or automatically, for example by setting a threshold of transmitted amplitude and comparison of values acquired at different points of the scanning relative to said threshold, very easily detects or displays in the figures anomalies from the amplitude transmitted via the piece which can correspond to defects in the internal structure of the objects examined. This method therefore identifies defects faster than methods proposed to date.

Also, once the gain corrections made for a given geometry are set, these corrections can be applied to all pieces of the same geometry. The inspection step 2000 can therefore be repeated for each new object to be 20 inspected, without the need to repeat step 1000.

According to a particular embodiment, the reference piece and the inspected object are axisymmetrical, that is, symmetrical in revolution about an axis, their surface resulting from the revolution of a line about the axis of symmetry. This is the case for example of a turbomachine blade casing.

The variations in thickness of such a piece in the radial direction about the axis are therefore identical over the entire circumference of the piece. In this respect FIG. 6 illustrates an example of a profile of variation in thickness of a turbomachine casing.

In this case, conducting initialisation step 1000 of the method can be simplified by determining a list of gain corrections to be made only for a radial profile of the piece, these gain corrections being transposable to the entire circumference of the piece.

Consequently, during scanning step 1100 of the reference piece by an ultrasound beam, the direction of exposure of the ultrasound beam is radial relative to the axis of symmetry, and the reference piece is scanned according to a line of said piece at the intersection of the surface of the reference piece with a radial plane. Advantageously, the reference piece is scanned according to a single line, but the scanning can also be repeated on several lines to verify the gain corrections obtained.

Next, during the inspection step 2000 of the object, all of the axisymmetrical object to be inspected is probed according to scanning lines of the ultrasound beam identical to the line of scanning made to set the gain corrections, by applying the corresponding correction to each point of said line.

The method is particularly adapted to inspection of turbomachine blade casings made of composite material to detect defects of porosities and delamination type in the material, including at the level of the flange for fixing the casing to other elements of the turbomachine, this flange having a bulk making its inspection impossible in the small radius (90° angle) and causing misalignment of probes causing signal loss.

FIGS. 7a and 7b illustrate a mapping obtained for the flange of a blade casing before and after application of gain corrections; the image obtained with corrected amplitude much more simply localises and dimensions the defects present in the piece.

Similarly, FIGS. 8a and 8b illustrate a mapping obtained for the casing, at the level of the stream of the latter, before and after application of gain corrections. The square defects in the structure of the casing are also much more visible.

The inspection method of objects proposed is not limited to a type of objects to be inspected in particular, but applies advantageously to blades of turbomachines or turbomachine blade casings, or to any other object having a complex geometry with many variations in thickness.

More generally, the invention applies to any object made of material having a high rate of absorption of the ultrasound, such as made of composite material, and in particular a woven 3D composite material or 3D interlock, that is, comprising a reinforcement structure taken into a matrix, for example in polymer material.

The method therefore easily controls these objects, and even immediately displays the defects they can comprise.

The invention claimed is:

1. An inspection method of an object (O) by ultrasound transmission, wherein a scanning of said object by an ultrasound beam and a measurement of an amplitude of the ultrasound beam transmitted via said object (O) are carried out, said measurement comprising conversion of the ultrasound beam into an electrical signal, applying an amplification gain to said electrical signal and said measurement of the amplitude of said electrical signal,
   to deduce therefrom a mapping in which each point of a projection surface of said object according to a direction of exposure is associated to the amplitude of the ultrasound beam transmitted to said point via said object, the method further comprising:
     carrying out said scanning and said amplitude measurement on a reference piece having a geometry identical to the object to be inspected, to deduce therefrom a mapping of said reference piece, the amplification gain applied for the amplitude measurement being a predetermined reference gain ($G_{ref}$),
     determining, for a plurality of points of the mapping of the reference piece, gain corrections to be made to said predetermined reference gain ($G_{ref}$) at the corresponding points of the scanning to obtain a constant amplitude of the ultrasound beam ($A_c$) transmitted via the reference piece for all the points of the mapping,
     carrying out said scanning and said amplitude measurement on the object to be inspected (O), by applying to the different points of the scanning an amplification gain ($G_c$) corresponding to said predetermined reference gain ($G_{ref}$) corrected from the gain corrections previously determined.

2. The method according to claim 1, wherein the mapping of the object is deduced from said amplitude measurement on the object to be inspected (O) and the resulting mapping is analysed to detect any anomaly as to the amplitude transmitted via the object.

3. The inspection method according to claim 1, wherein the object to be inspected and the reference piece are axisymmetrical, the direction of exposure of the ultrasound beam is radial relative to an axis of symmetry, and the reference piece is scanned according to a line of said reference piece at the intersection of a surface of the reference piece with a radial plane.

4. The inspection method according to claim 1, wherein the object to be inspected and the reference piece comprise composite material.

5. The inspection method according to claim 1, wherein the constant amplitude ($A_c$) transmitted via the reference piece is greater than 60% of the amplitude of the ultrasound beam emitted ($A_s$).

6. The inspection method according to claim 1, wherein the gain correction to be made to the predetermined reference gain ($G_{ref}$) at a point of the scanning is determined simultaneously with scanning of the corresponding point of the reference piece.

7. Use of the method according to claim 1, for inspection of a blade.

8. Use of the method according to claim 3, for inspection of a blade casing.

9. Use of the method according to claim 1, for inspection of a blade of a turbomachine fan, said blade being formed from composite material and also comprising a metal reinforcement stuck on a leading edge of said blade, said method detecting any adhesion anomalies.

10. An inspection system of an object by ultrasound transmission, for carrying out the method according to claim 1, comprising:
    an emission probe of the ultrasound beam and a control means for scanning of the probe, adapted for performing scanning of said object by the ultrasound beam emitted by the probe,
    an ultrasound receiver, adapted to convert the ultrasound beam transmitted via said object into an electrical signal, and
    a processing unit, comprising an amplifier adapted to apply an amplification gain to the electrical signal obtained by the receiver, and a control unit configured to measure an amplitude of the amplified electrical signal and to deduce from said amplitude measurement a mapping in which each point of a projection surface of said object according to a direction of exposure is associated to the amplitude transmitted to said point via said object,
    the system being characterized in that the control unit is further adapted to determine, for a plurality of points of a mapping performed from the scanning of a reference piece by the ultrasound beam at a predetermined reference gain ($G_{ref}$), gain corrections to be made to the predetermined reference gain ($G_{ref}$) at the corresponding points of the scanning to obtain a constant amplitude ($A_c$) transmitted via the reference piece for all the points of the mapping, and to control the amplifier in order to apply, during the scanning and said amplitude measurement on the object to be inspected, to the different points of the scanning of the ultrasound beam, an amplification gain ($G_c$) corresponding to the predetermined reference gain ($G_{ref}$) corrected as a function of the gain corrections thus determined.

11. The inspection method according to claim 6, wherein the constant amplitude ($A_c$) transmitted via the reference piece is between 70 and 90% of the ultrasound beam emitted ($A_s$).

12. The inspection method according to claim 6, wherein the constant amplitude ($A_c$) transmitted via the reference piece is equal to 80% of the ultrasound beam emitted ($A_s$).

* * * * *